United States Patent [19]

Malfroid

[11] 4,052,459
[45] Oct. 4, 1977

[54] PROCESS FOR THE MANUFACTURE OF ALKYLACETOPHENONES

[75] Inventor: Pierre Malfroid, Jemeppe-sur-Sambre, Belgium

[73] Assignee: Solvay & Cie, Brussels, Belgium

[21] Appl. No.: 594,223

[22] Filed: July 9, 1975

[30] Foreign Application Priority Data

July 16, 1974 France .................................. 74.25123

[51] Int. Cl.$^2$ ............................................. C07C 49/78
[52] U.S. Cl. .................................. 260/592; 260/668 R
[58] Field of Search ............................ 260/592, 668 R

[56] References Cited

U.S. PATENT DOCUMENTS

| 2,004,069 | 6/1935 | Bruson et al. ......................... 260/592 |
| 2,390,368 | 12/1945 | Hochwalt ............................ 260/592 |
| 2,802,812 | 8/1957 | Overberger ........................... 260/592 |
| 2,860,169 | 11/1958 | Schlatter ............................. 260/592 |

OTHER PUBLICATIONS

Mowry, J.A.C.S., vol. 68, pp. 1105-1109 (1946).

Primary Examiner—James O. Thomas, Jr.
Assistant Examiner—James H. Reamer
Attorney, Agent, or Firm—Spencer & Kaye

[57] ABSTRACT

A process for the manufacture of alkylacetophenones wherein (1) benzene is acylated, (2) the alkylaryl ketone thus obtained is hydrogenated catalytically, and (3) the alkylbenzene thus obtained is acetylated, in only one solvent chosen from among chlorinated aliphatic hydrocarbons containing 1 to 3 carbon atoms and 2 or 3 chlorine atoms per molecule, and their mixtures.

12 Claims, No Drawings

PROCESS FOR THE MANUFACTURE OF ALKYLACETOPHENONES

The present invention relates to an improved process for the manufacture of alkylacetophenones.

A known route for synthesising alkyl-substituted derivatives of acetophenone from benzene involves the following three reactions: (1) acylation of benzene to form an acylbenzene, (2) catalytic hydrogenation of the acylbenzene to form an alkylbenzene, and (3) acetylation of the alkylbenzene to form an alkylacetophenone.

The so-called Friedel-Crafts acylation reactions (1) and (3) can be carried out in solvents as diverse as carbon disulphide, benzene, petroleum ether, ethylene chloride and methylene chloride, carbon tetrachloride, nitrobenzene and nitroalkanes (Kirk-Othmer, Encyclopedia of Chemical Technology — second edition, volume 10, pages 163–164).

The catalytic hydrogenation reaction (2), on the other hand, is generally carried out in protonic solvents such as ethanol, as well as in saturated hydrocarbons such as hexane, decalin and cyclohexane. Acetic acid is preferably used (Thorpe's Dictionary of Applied Chemistry, fourth edition, volume VI, page 350).

In current practice, alkyl-substituted derivatives of acetophenone are thus manufactured from benzene by using two different solvents, namely a first solvent specific to Friedel-Crafts acylation reactions for the acylation (1) and the acetylation (3), and a second solvent, generally of protonic nature, for the catalytic hydrogenation (2). It is complicated and expensive to carry out this process which involves the complete removal of the solvent at the end of each step and the purification of the intermediate reaction products.

There has now been found in accordance with the present invention, a simplified process for the manufacture of alkylacetophenones from benzene, which employs only one solvent common to the three steps.

The present invention relates to a process for the manufacture of alkylacetophenones wherein (1) benzene is acylated, (2) the alkylaryl ketone thus obtained is hydrogenated catalytically, and (3) the alkylbenzene thus obtained is acetylated, in which the three reactions involving (1) acylation, (2) hydrogenation and (3) acetylation are carried out in only one solvent chosen from amongst chlorinated aliphatic hydrocarbons containing 1 to 3 carbon atoms and 2 or 3 chlorine atoms per molecule, and their mixtures.

By chlorinated aliphatic hydrocarbon, there are to be understood both saturated chlorinated aliphatic hydrocarbons and ethylenically unsaturated aliphatic hydrocarbons.

Although the use of chlorinated aliphatic hydrocarbons as a solvent medium for acylation reactions is known, it is, in contrast, surprising to find that the catalytic hydrogenation of the ketone group of alkylaryl ketones can be carried out easily and in good yields, generally of the order of 90% or more, in the chlorinated aliphatic hydrocarbons used in accordance with the process of the present invention.

It has moreover now been discovered that all chlorinated aliphatic solvents are not suitable for the catalytic hydrogenation of an alkylaryl ketone to form an alkylarene. Thus, for example, tetrachloromethane strongly inhibits the hydrogenation reaction and leads to acidification of the reaction medium, causing serious corrosion problems.

Chlorinated aliphatic hydrocarbons which are suitable for carrying out the process according to the invention are, for example, dichloromethane, trichloromethane, 1,2-dichloroethane, 1,2-dichloropropane and 1,1,2-trichloroethylene.

The chlorinated aliphatic hydrocarbons which are preferably used for carrying out the process of the invention are those which contain 2 chlorine atoms per molecule. The best results are obtained with dichloromethane, 1,2-dichloroethane and 1,2-dichloropropane, and more particularly with 1,2-dichloroethane. It should be noted that the use of these solvents in the form of mixtures also gives excellent results.

By solvent, there are thus to be understood hereafter the chlorinated aliphatic hydrocarbons according to the invention or their mixtures in any proportions.

The amount of solvent to be employed in each reaction of the process can vary to a rather large extent and is not particularly critical. It must nevertheless be sufficient to ensure that the solid reagents and the reaction products are completely dissolved during each reaction of the process.

The acylation of benzene (1) is advantageously carried out in the presence of an amount of solvent equal to 1.5 to 2 kg per kg of acylating reagent. The same amount of solvent is retained in order to carry out the hydrogenation reaction (2). The acetylation of the alkylbenzene is advantageously carried out in the presence of 1.5 to 2 kg of solvent per kg of alkylbenzene.

It is thus possible to retain the same amount of solvent from one end of the synthesis to the other and it is also possible to remove or add solvent at intermediate stages, provided that it is always guaranteed that the reagents and the reaction products are completely dissolved during each reaction of the process.

According to a preferential embodiment of the invention, 1.5 to 2 kg of solvent per kg of acylating reagent are used in the reaction (1) involving the acylation of benzene, the solution of alkylaryl ketone obtained is hydrogenated catalytically (2) without the intermediate addition or removal of solvent, the water formed during the catalytic hydrogenation reaction is removed by azeotropic distillation together with a part of the solvent, and the concentrated solution of alkylbenzene thus obtained is diluted by adding solvent in sufficient amount to bring the concentration back to 1.5-2 kg of solvent per kg of alkylbenzene before carrying out the reaction (3) involving the acetylation of the alkylbenzene.

The successive reactions involving (1) acylation, (2) hydrogenation and (3) acetylation of the process of the invention can be represented as follows:

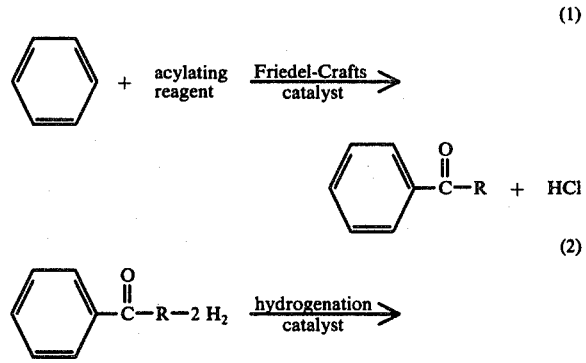

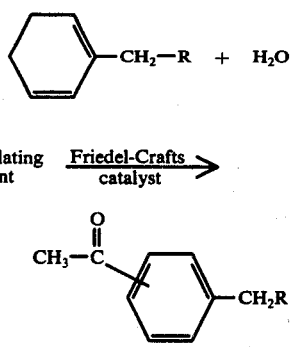

The product resulting from the acetylation reaction (3) consists, for the most part, of the para isomer.

The catalysts and the reagents employed in the present invention are those generally used for this type of reaction. Thus the usual catalysts for acylation reactions, such as aluminium chloride, aluminium bromide and boron trifluoride, are suitable for steps (1) and (3). It is, however, preferred to use aluminium chloride. This catalyst is used in approximately stoichiometric proportions relative to the acylating reagent.

For the catalytic hydrogenation, it is also possible to use the usual hydrogenation catalysts such as platinum metal or palladium metal, which may or may not be supported. According to a preferential embodiment of the present invention, a catalyst consisting of palladium metal fixed to active charcoal is used, and more particularly, such a catalyst containing of the order of 50 to 100 g of palladium metal per kg. It is advantageous to use the catalyst at the rate of approximately 5 g of palladium per kg of ketone.

The acylating reagent involved in the acylation reaction (1) is chosen in accordance with the alkyl radical which it is desired to fix to the acetophenone. By alkylacetophenone, there are to be understood, in this context, both alkylacetophenones in which the alkyl chain is linear or branched, and cycloalkylalkylacetophenones. The process of the invention can, in fact, be applied to the synthesis of any alkyl-substituted derivatives of acetophenone. It is especially suitable for the manufacture of alkylacetophenones corresponding to the general formula

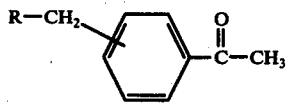

in which R is an aliphatic radical in which the total number of carbon atoms ranges from 1 to 24. It is more particularly suitable for synthesis of alkylacetophenones corresponding to the above general formula in which R is an aliphatic radical in which the total number of carbon atoms ranges from 3 to 19. An alkylacetophenone which is very particularly preferred is n-dodecylacetophenone.

The reagents used for the reaction (1) comprise the usual acylating reagents and especially anhydrides and chlorides of aliphatic organic acids.

The reagents which are used preferentially for the reaction (1) are aliphatic organic acid chlorides in which the total number of carbon atoms ranges from 2 to 25 and preferably from 4 to 20. An acid chloride which is very particularly preferred is lauroyl chloride.

The acylating reagent is employed in approximately stoichiometric proportions relative to benzene.

Finally, any of the usual acetylating reagents, and especially acetic anhydride and acetyl chloride, are suitable for carrying out the reaction (3). It is nevertheless preferred to use acetic anhydride which is less expensive than the corresponding chloride. In this case, approximately two mols of Friedel-Crafts catalyst are employed per mol of acetic anhydride.

The temperature and pressure conditions for the three reactions of the process of the invention are the usual conditions and are not critical.

For reasons of convenience, the acylation and acetylation reactions (1) and (3) are advantageously carried out under atmospheric pressure at a temperature generally between 0° and 100° C, and preferably between 25° and 50° C.

Likewise, the catalytic hydrogenation is preferably carried out at a temperature of between 20° and 120° C, and more particularly of approximately 60° C. The pressure can rise to a value of between 1 and 20 atmospheres; in practice, it is advantageously some 10 atmospheres.

The order in which the reagents are introduced is not critical. In the acylation reaction (1), the original constituents of the medium are preferably introduced in the following order, namely solvent, catalyst, acid chloride and benzene. The extent to which the reaction has taken place can be checked, for example, by chromatographic determination of the organic acid (derived from the acid chloride) present after hydrolysis in samples removed from the reactor.

When the desired degree of conversion is reached, the catalyst is decomposed by introducing the reaction mixture into an aqueous acid solution, for example a solution of hydrochloric acid.

After decanting, the aqueous phase, made heavier by the metal salts of the catalyst, forms the lower layer. The acid organic phase, consisting mainly of a solution of alkylaryl ketone in the reaction solvent, is then neutralised in a manner which is in itself known before being hydrogenated catalytically.

After the hydrogenation reaction (2), carried out under the general conditions described above, the water produced as well as the excess benzene from the acylation reaction and the majority of the reaction solvent are removed by rectification, optionally under reduced pressure. As indicated above, the removal of part of the solvent is advantageous at this stage, in that it makes it possible to distil azeotropically the water formed during the hydrogenation reaction and to obtain concentrated solutions of the alkylbenzene. After removal of the water, the recovered solvent can be recycled to the manufacturing process.

The acetylation reaction (3) is carried out thereafter in accordance with a process similar to that described above for reaction (1), involving the introduction, in the following order, of the solvent, preferably in an amount sufficient to bring the concentration of the solution back to 1.5–2 kg of solvent per kg of alkylbenzene, the catalyst, the acetylating reagent and the solution of alkylbenzene which may have been concentrated and was obtained on rectification after hydrogenation. After destroying the catalyst, as described above, an acid organic phase which consists of a solution of the alkylacetophenone in the reaction solvent is obtained. It is not absolutely necessary to neutralise this organic phase. It suffices, for example, to evaporate it under reduced pressure in order to remove the solvent as well as the acetic and hydrochloride acids which it can also contain, in order to recover the alkylacetophenone in solid form.

The alkylacetophenones manufactured in accordance with the process of the present invention form intermediate products for the synthesis of α-(alkylphenyl)-indoles which are particularly effective heat stabilisers for vinyl resins, and in particular for polyvinyl chloride.

The manufacture of α-(alkylphenyl)-indoles corresponding to the general formula

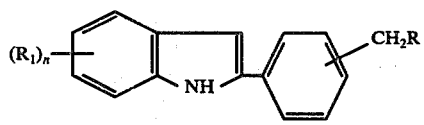

in which R is an aliphatic radical in which the total number of carbon atoms is between 3 and 19 and $R_1$ is an aliphatic radical in which the number of carbon atoms is between 4 and 20, by condensation of an alkylacetophenone with a phenylhydrazine, followed by cyclisation in an acid medium, as well as their use as stabilisers for vinyl resins, are described in French Patent Application No. 72/32,076 of Sept. 8, 1972 in the name of Solvay & Cie.

The following examples illustrate the invention without however limiting it.

Examples 1 and 2 relate to the manufacture of n-dodecylacetophenone in 1,2-dichloroethane and in dichloromethane respectively.

EXAMPLE 1

Acylation (1)

Manufacture of laurophenone starting from benzene and lauroyl chloride. The manufacturing process is carried out in a 5 liter thermostatically controlled reactor equipped with a stirrer, a thermometer, a condenser extended by a hydrogen chloride absorbing device, a graduated dropping funnel and a device for introducing nitrogen. The apparatus is evacuated and then flushed with nitrogen three times so as to drive out all the air present in the flask and the dropping funnel.

1,000 g of 1,2-dichloroethane and 293 g, corresponding to 2.2 mols, of aluminium trichloride are introduced successively into the reactor, with stirring. 459 g, corresponding to 2.1 mols, of lauroyl chloride are then introduced rapidly into the resulting suspension, taking care that the temperature of the medium does not exceed 30° C. The medium is stirred for approximately 30 minutes until the aluminium chloride has dissolved completely.

172 g, corresponding to 2.2 mols, of benzene are then introduced at a rate such that the temperature of the medium does not exceed 40° C. When the introduction of benzene is complete, the medium is kept at 40° C for a further 1 hour.

The activity of the catalyst is then destroyed, without delay, by introducing the reaction mixture, with stirring, into 1 liter of a concentrated solution of hydrochloric acid (10 to 12 mols/liter). The temperature rises to about 55° C and the mixture becomes pasty. After having stirred this mixture for 30 minutes, 1 liter of water is introduced therein. The mixture becomes clear and is heated under reflux. The upper organic phase is isolated by decanting: it is clear, of a light brown colour, and contains 356 g/kg of laurophenone. The yield of laurophenone is as much as 89%.

Hydrogenation (2)

Manufacture of dodecylbenzene by catalytic hydrogenation of laurophenone.

The solution of laurophenone in 1,2-dichloroethane obtained in the first step is passed through a column containing calcium carbonate, in order to neutralise the acidity.

1,200 g of the said neutralised solution, corresponding to 1.64 mols of laurophenone, are introduced into a stainless steel autoclave from which the air has been driven by means of nitrogen, together with 42 g of a catalyst consisting of palladium metal fixed to active charcoal, containing 50 g of metal per kg. The autoclave is heated to 60° C. Hydrogen at a pressure of 10 kg/cm² is then introduced into the medium which is stirred. Hydrogen ceases to be consumed after approximately 3 hours. The autoclave is then cooled and the hydrogen is driven out by means of nitrogen. After filtering off the catalyst, a clear organic solution is obtained which has a slight yellow colour and contains 321 g/kg of dodecylbenzene. The conversion of laurophenone is practically complete.

The water formed during the hydrogenation reaction is removed by azeotropic distillation together with part of the 1,2-dichloroethane, and a concentrated solution containing 91% by weight of dodecylbenzene is thus obtained.

Acetylation (3)

Acetylation of dodecylbenzene to form dodecylacetophenone.

The acetylation reaction is carried out in an apparatus and in accordance with a procedure similar to those described in the first reaction.

900 g of 1,2-dichloroethane and 480 g, corresponding to 3.6 mols, of aluminium chloride are introduced successively, with stirring, into the reactor which has been flushed with nitrogen. 199 g, corresponding to 1.95 mols, of acetic anhydride are then introduced into the resulting suspension, taking care of that the temperature does not exceed approximately 30° C. The medium is stirred at approximately 30° C for some 30 minutes until the aluminium chloride has dissolved completely.

406 g of the concentrated solution of dodecylbenzene in 1,2-dichloroethane obtained in the preceding step, which corresponds to 1.5 mols of dodecylbenzene, are then introduced gradually, keeping the temperature below 30° C. When the introduction of dodecylbenzene is complete, the temperature of the medium is raised to 40° C and is kept at this temperature for 2 hours. At the end of this period of time, evolution of hydrogen chloride, originating from the side reaction between the acetic acid formed and aluminium chloride, has practically ceased. The reaction mixture is then poured slowly into 2 liters of hydrochloric acid (6 to 7 mols/liter) in order to destroy the catalyst. The resulting mixture is heated under reflux for 1 hour. After the upper organic phase has been isolated by decanting, it is evaporated under reduced pressure. The solid collected is slightly brownish. This product consists of the para isomer together with small amounts of impurities. The composition, determined by gas phase chromatographic analyses and by gel permeation, is as follows:

| | |
|---|---|
| Para-dodecylacetophenone | 931 g/kg |
| 1-Phenyldodecane | 1.2 g/kg |
| Dodecylacetylcyclohexane and unidentified products | 45 g/kg |
| Non-volatile products | 23 g/kg |

The yield of p-dodecylacetophenone is as much as 92%.

The crude p-dodecylacetophenone can be used directly, without prior purification, for the synthesis of α-(p-dodecylphenyl)-indole.

EXAMPLE 2

This example relates to the manufacture of dodecylacetophenone in dichloromethane.

The apparatus and the general procedure are those described in Example 1. Because the boiling point of dichloromethane is lower, it is however advisable to keep the temperature below 40° C during the first and the third reactions.

Acylation (1)

In this case, 1,200 g of dichloromethane are used. The reagents and the catalyst are used in the amounts indicated in Example 1. At the end of the reaction, after destroying the catalyst and isolating the upper organic phase, a solution of laurophenone in dichloromethane, containing 320 g/kg of laurophenone, is obtained. The yield of laurophenone is as much as 93%.

Hydrogenation (2)

1,400 g of the neutralised organic solution obtained in the preceding step, corresponding to 1.72 mols of laurophenone, are hydrogenated catalytically in the presence of 22.4 g of the same hydrogenation catalyst. The reaction is complete after 30 minutes. The conversion of laurophenone is practically complete. The water is removed by azeotropic distillation in order to obtain a concentrated solution containing 90% by weight of dodecylbenzene.

Acetylation (3)

900 g of dichloromethane and 460 g, corresponding to 3.45 mols, of aluminium chloride are introduced into the reactor used in the first step. Thereafter, 168 g, corresponding to 1.65 mols, of acetic anhydride and 411 g of the concentrated solution of dodecylbenzene in dichloromethane obtained in the preceding step, which corresponds to 1.5 mols of dodecylbenzene are introduced into the reactor.

I claim:

1. In a process for the manufacture of alkylacetophenones wherein (1) benzene is acylated by means of an acylating agent selected from the group consisting of anhydrides and chlorides of aliphatic organic acids in order to obtain an alkylphenylketone, (2) the alkylphenylketone thus obtained is hydrogenated catalytically in order to obtain the corresponding alkylbenzene and (3) the alkylbenzene thus obtained is acetylated by means of an acetylating agent selected from the group consisting of acetic anhydride and and acetyl chloride in order to obtain the corresponding alkylacetophenone, the improvement wherein the three reactions involving (1) alkylation, (2) hydrogenation and (3) acetylation are carried out in only one solvent selected from the group consisting of chlorinated aliphatic hydrocarbons containing 1 to 3 carbon atoms and 2 or 3 chlorine atoms per molecule, and their mixtures.

2. Process according to claim 1, wherein the sole solvent is selected from the group consisting of chlorinated aliphatic hydrocarbons containing 2 chlorine atoms per molecule, and their mixtures.

3. Process according to claim 2, wherein the sole solvent is selected from the group consisting of dichloromethane, 1,2-dichloroethane, 1,2-dichloropropane, and their mixtures.

4. Process according to claim 2, wherein the sole solvent is 1,2-dichloroethane.

5. Process according to claim 2, wherein the sole solvent is dichloromethane.

6. Process according to claim 1, wherein 1.5 to 2 kg of solvent per kg of acylating reagent are used in the reaction (1) involving the acylation of benzene, the solution of alkylaryl ketone thus obtained is hydrogenated catalytically in the reaction (2) without the intermediate addition or removal of solvent, the water formed during the hydrogenation reaction together with a part of the solvent are removed, and the concentrated solution of alkylbenzene thus obtained is diluted by adding solvent in sufficient amount to bring the concentration back to 1.5 to 2 kg of solvent per kg of alkylbenzene before carrying out the reaction (3) involving the acetylation of the alkylbenzene.

7. Process according to claim 1, wherein an acylating reagent used for the reaction (1) involving the acylation of benzene is an aliphatic organic acid chloride containing 2 to 25 carbon atoms.

8. Process according to claim 7, wherein the aliphatic organic acid chloride contains 4 to 20 carbon atoms.

9. Process according to claim 8, wherein the aliphatic organic acid chloride is lauroyl chloride.

10. Process according to claim 1, wherein the catalytic hydrogenation reaction (2) is carried out in the presence of a catalyst consisting of palladium metal fixed to active charcoal.

11. The process according to claim 1, wherein in the reaction (2), platinum metal or palladium metal is used as a hydrogenation catalyst.

12. The process according to claim 1 wherein in the acylation step (1) and the acetylation step (3), a catalyst is used which is selected from among aluminum chloride, aluminum bromide and boron trifluoride.

* * * * *